(12) United States Patent
Calavrezos et al.

(10) Patent No.: US 11,185,217 B2
(45) Date of Patent: Nov. 30, 2021

(54) DRAPE FOR ENDOSCOPIC CAMERA AND CONTAINER

(71) Applicant: Promecon GmbH, Hamburg (DE)

(72) Inventors: Alexander Calavrezos, Hamburg (DE); Lenika Calavrezos, Hamburg (DE); Philipp Kraus, Hamburg (DE)

(73) Assignee: Promecon GMBH

( * ) Notice: Subject to any disclaimer, the term of this patent is extended or adjusted under 35 U.S.C. 154(b) by 20 days.

(21) Appl. No.: 16/534,368

(22) Filed: Aug. 7, 2019

(65) Prior Publication Data

US 2020/0046207 A1 Feb. 13, 2020

(30) Foreign Application Priority Data

Aug. 9, 2018 (EP) .................................... 18188207

(51) Int. Cl.
*A61B 1/00* (2006.01)
(52) U.S. Cl.
CPC ................... *A61B 1/00142* (2013.01)
(58) Field of Classification Search
CPC ... A61B 1/00; A61B 1/00142; A61B 1/00144; A61B 1/00064; A61B 1/00066; A61B 1/0011
USPC ........................................ 206/363, 364, 233
See application file for complete search history.

(56) References Cited

U.S. PATENT DOCUMENTS

| | | | | |
|---|---|---|---|---|
| 5,078,483 A * | 1/1992 | Herzberg | ........... | A61B 1/00142 359/510 |
| 5,325,846 A * | 7/1994 | Szabo | ................ | A61B 1/00142 206/303 |
| 5,971,916 A * | 10/1999 | Koren | ................... | A61B 46/10 359/510 |
| 6,123,080 A * | 9/2000 | Mohan | .................. | A61B 46/10 128/849 |
| 7,585,268 B2 * | 9/2009 | Cheich | ................ | B31D 5/0043 206/233 |

(Continued)

FOREIGN PATENT DOCUMENTS

JP 2017074984 A 4/2017

OTHER PUBLICATIONS

European Search Report for application No. EP18188207.7, dated Feb. 15, 2019, 8 pages.

*Primary Examiner* — Rafael A Ortiz
(74) *Attorney, Agent, or Firm* — Kacvinsky Daisak Bluni PLLC

(57) ABSTRACT

An embodiment herein includes a device comprising a tubular drape for covering surgical equipment and furthermore comprising a container adapted to accommodate a substantial portion of the drape in an axially compressed state in a ring-shape, the container comprising a first sheet and a second sheet, wherein the first sheet and the second sheet are oppositely arranged, the first sheet having a first opening and the second sheet having a second opening, wherein the first opening is configured for withdrawal of the drape from the container, and wherein the first and the second openings are configured for passing the surgical equipment to be covered therethrough, wherein the accommodated ring-shaped drape portion has a mechanical stiffness substantially contributing to the overall stiffness of the device. A method for manufacturing a device comprising a tubular drape and a container is disclosed herein.

20 Claims, 10 Drawing Sheets

(56) References Cited

U.S. PATENT DOCUMENTS

| | | | |
|---|---|---|---|
| 2012/0283663 A1* | 11/2012 | Delegge | A61M 25/0111 604/264 |
| 2013/0023920 A1* | 1/2013 | Terliuc | A61B 1/0011 606/192 |
| 2014/0066711 A1* | 3/2014 | Farin | A61B 1/04 600/109 |
| 2016/0066770 A1* | 3/2016 | Barbato | A61B 1/00167 600/138 |
| 2017/0280988 A1* | 10/2017 | Barbato | A61B 1/018 |

* cited by examiner

DRAPE FOR ENDOSCOPIC CAMERA AND CONTAINER

CROSS-REFERENCE TO RELATED APPLICATIONS

This application claims the benefit of priority under 35 U.S.C. § 119 to European Patent Application No. 18188204.7, filed Aug. 9, 2018, entitled "Drape for Endoscopic Camera and Container," which application is incorporated herein by reference in its entirety.

FIELD

The present disclosure relates a tubular drape for covering an endoscopic camera and a container for storage of and dispensing of such drape.

BACKGROUND

Modern surgical endoscopes can be connected to video cameras in order to generate and display an image. For this purpose, e.g., the international standard ISO/TS 18339:2015 (en) "Endotherapy devices—Eyepiece cap and light guide connector" specifies the design of the eyepiece cap and the light guide connector of an endoscope to enable the combination of products from different manufacturers. The eyepiece cap is the part of the endoscope located at the proximal end of the endoscope to which a photographic or video camera can be attached. As specified by said standard, the eyepiece has a generally conical shape with a lumen for optical image transmission. There may be similar specifications in other standards.

While the endoscope can be sterilized, a camera for use with the endoscope may not be sterile. In order to maintain surgical sterility, the camera can be covered or enclosed by a sterile drape or the like. One way of covering the camera may be by attaching a drape, such as a tubular plastic film to the eyepiece cap and enclosing the camera. Couplers may be used to maintain the sterile barrier when changing the endoscope. With such a coupler, the endoscope may be exchanged during an ongoing surgery while maintaining the sterile barrier.

Independent of the use of a coupler, the application of the drape in the surgical environment may be challenging, considering the risk of breaking the sterile barrier or creating a barrier which may not be sterile in the first place. When covering a camera with an attached cable with a tubular drape, this drape needs to be drawn over the camera while upholding sterility at the required places.

A tubular drape comprising a sleeve and a ring-shaped former is a known configuration. A proximal region of the drape is mounted on a radial outer periphery of the tubular former with a snug fit in multiple layers, wherein the drape (sleeve) can be retrieved from the tubular former by pulling it off, layer for layer. This solution, however, may have the challenges of a complex and expensive multi-part tubular former, a complex and expensive assembly procedure in order to wind the snug-fit onto the former. In use, this solution may have the further challenge of a fixed-geometry former, the diameter of which irreversibly defining the devices compatibility with surgical equipment to be covered.

Other tubular drapes may have the substantial drawback in that the tubular drape needs to be removed in the direction of the endoscope because the equipment covered by drape cannot be passed therethrough. A further challenge may be the complex mounting procedure involving subsequent withdrawal of both ends of a tubular drape from a container. Furthermore, this drape may not be compatible with camera coupler devices.

SUMMARY

The present disclosure aims at overcoming or at least minimizing these challenges. The present disclosure is not limited to endotherapy and the embodiments described here may be applied in all fields of endoscopy. In particular, this disclosure may provide a device for reliably creating a sterile operation theater and allowing easy and safe application of a tubular drape to cover surgical equipment. Furthermore, the present disclosure aims at providing a method for manufacturing a device comprising a tubular drape and a container in an economic and reliable manner.

The present disclosure relates to embodiments of a device comprising a tubular drape for covering surgical equipment and a container, e.g., configured to accommodate a substantial portion of the drape in an axially compressed state in a ring-shape, the container being radially inwardly open, and embodiments of methods for manufacturing a device comprising a tubular drape and a container.

In embodiments, the present disclosure relates to a device that may be used for covering surgical equipment such as cameras for endoscopic use and camera cables. When attaching a camera to a camera port of an endoscope, the image signal transmission cables may extend from the camera to an image display device, such as a computer with display. Therefore, surgical equipment comprising a camera and camera cables may have a generally elongate geometry and may flex during use. A tubular drape, especially an elongate tubular drape, of a flexible material may therefore be suited for covering such surgical equipment in some embodiments. In order to create a sterile barrier, the drape may be connected or attached to an endoscope or an intermediate part such as a coupler and may comprise a sterile barrier side (facing into the operating room) and a non-sterile barrier side (facing towards the camera and/or cable(s)).

When applying or mounting a tubular drape to the surgical equipment to be covered, the tubular drape may be drawn or pulled over the equipment, starting at one end, in a relative movement until the surgical equipment may be covered in an appropriate way.

Devices according to the disclosure may comprise a container configured to accommodate a substantial portion of the drape in an axially compressed state. A substantial portion of the drape may be a portion of the drape extending along the tubular axis of the drape from a starting point up to an end point. Typically, this may be more than 50%, more typically more than 70%, and more typically more than 90% of the drape in an axial direction. Such substantial portion may or may not comprise one or both ends of the tubular drape. The container may be configured to accommodate a substantial portion of the drape including one drape end. When accommodated, said portion of the drape may be positioned within the container geometry.

In an axially compressed state, the tubular drape may be compressed in the direction of the tubular axis. In other words, a drape portion may not fully extend in axial direction when it is in a compressed state, compared to an extended state. This compression may be realized by folding, stuffing, cramming, crumpling or the like. This compression may be realized by a concertina style folding. A portion of the drape in an axially compressed state in a ring shape may have a geometry generally similar to a geometric torus, having an outer periphery and an inner periphery leaving an opening inside the inner periphery. The ring-shape may have a generally circular shape like a torus, or an elliptical shape, or a polygonal shape or a combination thereof. A ring-shape may be realized by multiple folded layers of tubular drape generally transverse or orthogonal to the tubular axis, wherein these layers are stacked on one another in an axial direction. Instead or in combination therewith, a ring-shape may be realized by multiple folded layers generally parallel to a drape tube perimeter wall, wherein these layers are stacked on one another in a radial direction. A ring-shape may also be realized by cramming the drape into a ring-shaped geometry. Thereby, a multitude of asymmetric layers or wrinkles may form a ring-shape. The container may apply forces in an axial direction corresponding to compression forces of the drape. The container may direct the forces from one side to the opposite container side in an axial direction. An axial compression may contribute to hold the drape within the container. Compression forces in axial direction may result in frictional forces in a radial direction.

The container may be inwardly open. An inwardly open container may be at least partly open towards the inside of the container. There may be a free space between a portion inside the container close to its outer periphery and the inner core of the container. This free space may communicate with the outside of the container, via a first container opening, in some embodiments. If, for example, the container has a generally cylindrical outer shape, there may be a space between the inside of the outer cylinder wall and the axis of the cylinder, and this space may allow communication therebetween. If, however, this container with generally cylindrical outer shape additionally has an inner geometry with a cylindrical wall extending fully along the axis of the outer cylinder, then the inner cylindrical wall may block communication between the inside of the outer cylindrical wall and the axis of the cylinder. As a further example, a container with the closed shape of a torus may not be inwardly open, because the inner torus wall blocks communication between the inside of the outer torus wall and the torus axis and because it may not allow communication with the outside of the container. A container with generally cylindrical outer shape may have a mandrel extending along only a part of the axis of the cylinder, leaving a space where it does not extend along the axis of the cylinder for the container to be inwardly open. If, however, the mandrel extends along the axis up to or beyond both cylinder ends, then this container may not be inwardly open.

The drape may be made of a film and/or textile material. A film material may be a plastic film material such as, e.g., polyethylene or polyvinyl chloride. It may be a textile material or film and textile, such as a composite coated textile material. These materials may be beneficial for the drape to be a sterile barrier and to allow movement of the surgical equipment covered. A film and/or textile material may be suited for compression of the drape in axial direction in a ring-shape.

The container may comprise a first sheet and a second sheet, wherein the first sheet and the second sheet are oppositely arranged, the first sheet having a first opening and the second sheet having a second opening. A sheet may extend further in two dimensions (width and length) than in a third dimension (height). A sheet may be flexible, thereby possibly taking on different shapes. A sheet may also be of a solid and/or stiff material. It may be flat in a planar sense or it may be flexed, bent, molded or otherwise shaped in three dimensions. The first sheet and the second sheet may be made of a film material and/or one or more thermoformed sheets. Such film material may be a foil, a paper, a pasteboard, a cardboard or another material. The first sheet and the second sheet may be individual parts, they may also be portions of other parts or they may be integrally shaped, even with both sheets formed in one integral part. The first and the second sheet may be made from one sheet. The sheets may form ends of the container in the two axial directions. The sheets may delimit an accommodated drape portion in axial direction. The container may comprise one sheet made of a thermoformed sheet and the second sheet made of a film material, the thermoformed sheet being deep-drawn or otherwise thermoformed in an axial direction with respect to the tubular axis of an accommodated drape. An opening may be an omission of sheet material, such as a hole. Such opening may be circular, elliptical, polygonal or a combination thereof.

The first sheet and/or the second sheet may be made from a flexible material so that the container may be configured to compress an accommodated ring-shaped portion between the first sheet and the second sheet. A flexible sheet may flexibly react to the accommodated drape portion and adapt its shape. This shape may vary, depending on the degree and technique of compression. At the same time, the compression may vary depending on the material and shape of the container.

The first opening may be configured for withdrawal of the drape from the container. When a portion of the drape is accommodated within the container, the portion or a subportion thereof may be withdrawn from the container by moving it through the first opening. A diameter of the first opening may be smaller than a diameter of the tubular drape in a radially extended state. In that case, the drape may be locally and temporarily radially compressed or tapered in order to pass through the first opening. The first opening may resemble a bottleneck in this case, the drape to be threaded through the bottleneck. If a sub-portion of the drape is withdrawn through the first opening, the remainder may remain inside the container. A withdrawal may take place in a discrete layer-by-layer manner or in a continuous manner. Withdrawal may be realized by pulling a drape portion which may not be accommodated inside the container away from the container in a direction similar or equal to the direction of the tubular axis. Withdrawal may be limited by attaching the drape to the container or unlimited, allowing full withdrawal of the drape. The same may apply to the second opening, in this case with withdrawal of the drape in the opposite direction compared to the first opening. Frictional forces may apply between the container and the drape. Specifically, frictional forces may apply between an accommodated portion to be withdrawn and the first sheet. The accommodated drape portion may be in a compressed state, with compression forces corresponding to forces between container and drape in axial direction. Compression forces in axial direction may mechanically influence the frictional forces of withdrawal. As the drape is withdrawn and as less drape sub-portions remain accommodated within the container, the compression force may decrease. Correspondingly, frictional forces may decrease.

The first and the second opening may be configured for passing the surgical equipment to be covered therethrough. When applying the tubular drape over an elongate surgical equipment in the direction of the tubular axis, this may involve or require withdrawal of an accommodated portion of the drape from the container. This may be realized by placing the container at a position relative to the equipment, e.g. one end of the equipment, and then withdrawing the drape in the direction of the equipment with an end of the drape first. Instead, a drape end may be held relative to the equipment or attached to the equipment wherein the container may be pulled over the elongate equipment, thereby withdrawing drape sub-portions continuously while pulling the container away from the drape end. For this purpose, the first and the second opening may be configured for passing the surgical equipment to be covered therethrough. The first and the second opening may be circular. They may have a diameter larger than that of equipment to be covered. They may be configured for both the drape and surgical equipment to pass therethrough. In particular, in case of a bottleneck configuration, the drape may be between the opening and the surgical equipment in a radial direction. The openings may be variable or flexible, adapting to cross sectional geometries of surgical equipment passing therethrough.

An accommodated ring-shaped portion may define an axis and an opening of the accommodated ring-shaped portion may be configured for passing the surgical equipment therethrough. The opening of the accommodated ring-shaped portion may be substantially circular or elliptical. The opening shape may be influenced by a multitude of layers or wrinkles of accommodated drape in a compressed state. A diameter of the opening in at least one direction may be larger than that of equipment to be covered and passed therethrough.

The opening of the accommodated ring-shaped drape portion, the first opening and the second opening may be substantially aligned relative to the axis. Their axes may be coaxial, meaning parallel and positioned identically or substantially parallel and substantially close to each other with intersections at the device. Aligned axes may be beneficial for and facilitate passage of surgical equipment therethrough. Aligning the opening of the ring-shaped drape portion and the first opening may be beneficial for the withdrawal of the drape therethrough. The first opening may be a bottleneck for the drape, and the drape may thread well therethrough when aligned therewith.

The first sheet may comprise a dispensing lip at an edge region of the first opening. The dispensing lip may be open or closed or may include multiple lips. It may be circular or elliptical or polygonal. The lip may be flexible and may adapt when forces are applied, yet the dispensing lip does not tear, e.g., along any perforations or the like, in some embodiments. It may be closed and resist tensile forces. The dispensing lip may, when in a bottleneck configuration, and a drape is threaded therethrough, withstand forces applied in radial and/or axial directions. In combination with a first sheet and a second sheet the dispensing lip may both uphold compression forces in axial direction and at the same time allow retrieval of the drape. The dispensing lip may be configured to provide friction when in contact with another material, e.g., the drape. The dispensing lip may be of an elastic or non-elastic material. The first sheet may comprise an attachment portion located radially outside of or away from the dispensing lip, wherein the attachment portion may connect the first sheet with the second sheet. The second sheet may have a corresponding attachment portion. The container may comprise a cylinder member, the cylinder member being generally cylindrical and connecting the first sheet and the second sheet. Instead, the attachment portion may directly connect the first and the second sheet, the first and the second sheet may together form the body of the container. The attachment portion may circumferentially surround the dispensing lip.

A first end of the drape may be attached to the container and/or a first end of the drape may be inside the container and the other end of the drape may be free to be coupled with surgical equipment or attached to a coupler for coupling surgical equipment to a camera. The first end may be part of a portion of the drape accommodated in the container. The other end may be free to be coupled with surgical equipment, meaning not accommodated inside the container and therefore not withdrawn. The withdrawal of drape from the container may be realized by pulling the other end away from the container until a part of or the entire drape is withdrawn. When the drape is (almost) fully withdrawn from the container, an attachment between the two may prevent separation. Such separation may be undesirable during operation because such an event could hinder the process of reliably constructing a sterile barrier between camera and surgical environment. When the first end of the drape is inside the container and attached to the container, it may be attached to a place inside the container and/or between the first and the second sheet. The drape may be threaded from inside the container through the second opening (e.g., a second bottleneck) for attachment to the outside of the container. In the latter case, the first end may be attached to the container but not inside the container. The first end of the drape may not be tubular, deviating from its otherwise geometry. The first end of the drape may comprise one or more joining flanges, which may be attached to the container. The joining flanges may be formed from the tubular drape by cutting or otherwise forming one or more slots in the first end of the tubular drape. The other end of the drape may be attached to a camera coupler or other surgical equipment.

Devices may comprise a handling portion. A handling portion may be a portion of the container configured for manual grasp. It may also be separate part connected to the container. The handling portion may be formed by the container, in some embodiments by the first sheet and/or the second sheet. The first and second sheets may be attached radially outside of an accommodated ring-shaped drape. The first and the second sheets may be attached in a parallel or coplanar way. The first and the second sheets may extend radially beyond their attachment portion to form one or more handling portions radially outside of an accommodated ring-shaped drape. The handling portions may be two handling portions arranged oppositely, suited for grasp with one hand each.

The handling portion may comprise a non-sterile portion. A non-sterile portion may be a portion to be grasped by non-sterile surgical staff. In the surgical context, creating a sterile barrier may require differentiation between sterile and non-sterile areas. In the example of elongate covering surgical equipment with a tubular drape, a relative movement between the equipment and the drape may be required. If, for example, surgical equipment to be covered is not sterile but needs to be grasped and handled, then these non-sterile hands must not touch sterile parts of the drape, specifically the outside of the tubular cover. Non-sterile areas on the device may aid in clearly and safely creating the sterile barrier by clearly indicating where which hand may grasp. A non-sterile area may, e.g., be indicated by a color deviating from sterile areas.

Devices may also comprise a mandrel. A mandrel may have a cylindrical shape and may be radially inside of an accommodated ring-shaped drape portion. The mandrel may delimit the ring-shaped drape in radially inward direction, defining the opening at that position. It may be of a flexible or rigid material. The mandrel may leave an opening between the mandrel and the first opening for drape to pass when withdrawn. For the container to be inwardly open, the mandrel may not extend axially up to or beyond both ends of the container or up to or beyond both the first sheet and the second sheet without leaving an opening. The disclosure does not necessarily and generally require a mandrel. It may, however, be useful in the above-described context.

The container may have a ring-shaped dispensing opening. The ring-shaped dispensing opening may be formed between an outside of an inner core of the container and an inner circumference of a dispensing lip of an outer container part. An inner core of the container may be radially inward with respect to an outer container part. The inner core may have a ring-shape. The inner core may be a container mandrel. An axis of the inner core and an axis of an outer container part may be aligned. An outer container part may be formed by a first sheet and/or a second sheet. A dispensing opening may be ring-shaped when an inner core limits on the inside and an outer container part limits it on the outside with respect to a ring axis. A ring-shaped opening may be a ring-shaped gap between an outer container part and an inner core of the container. An outside of an inner core may be the outer circumference of an inner core of the container.

A ring-shaped dispensing opening may correspond to a first opening in a first sheet. A dispensing lip of an outer container part may correspond to a dispensing lip at an edge region of the first opening. An inner core may be integrally formed with a second sheet. An inner core may extend in a direction of a container axis within the limits of a first sheet and a second sheet, it may also extend beyond a first sheet and/or beyond a second sheet in an axial direction.

The first sheet and the second sheet and/or further container parts may be adhesively connected or welded together. This may be done, for example, by thermo welding or ultrasonic welding. An adhesive connection may apply glue or other means of adhesion like an adhesive film. This connection may be established by means of a closed seam, in some embodiments a seam circumferentially surrounding an accommodated ring-shaped drape. A seam surrounding, e.g., closely surrounding, an accommodated drape may have the advantage of limiting lateral movement of the drape and defining the ring-shape and/or its compression. In some embodiments, the seam may be open or split into multiple seams. The sheets may form handling portions which may comprise further seams. Further container parts may also be connected. The drape, in some embodiments a drape end, may also be connected. One or more joining flanges of the drape may be connected, e.g., welded in between the first and the second sheet.

The accommodated ring-shaped drape portion may have a mechanical stiffness substantially contributing to the overall stiffness of the device. Depending on the degree of the compression and its construction of layers, an accommodated ring-shaped drape portion may in itself or with its surrounding container provide a noteworthy stiffness. Thus, while the container may be otherwise flexible, e.g., because it comprises flexible sheets, the stiffness of the ring-shaped accommodated drape portion may substantially contribute to the overall stiffness of the device. In particular, the ring-shaped accommodated drape portion may be the stiffest component of the overall device. For example, in embodiments, the stiffness of the ring-shaped drape portion as such may be at least so that it does not deform substantially or not at all when held at one arbitrary part of the ring, i.e., the opposite side from where it is held does not deform downwardly due to the influence of gravity, and also not when an additional mass, e.g., of 50 g or 100 g, may be applied to said opposite portion. This feature may reduce the mechanical requirements and thus the complexity and the costs of the container and allows for the use of, for example, flexible materials as container parts.

The shape of the tubular drape may not be restricted to a tube in the sense of a cylinder with circular cross section. Moreover, the tubular drape may have an elliptical, a polygonal cross section or a combination thereof. The drape may also be a "layflat" tubular drape. Such layflat tubular drapes may be between 120 mm and 170 mm wide. Accordingly, the accommodated ring-shaped drape portion, the first and the second opening may not be restricted to strictly circular cross-sections. A combination of geometries between the parts may have additional advantages with respect to the withdrawal mechanism, the compression and accommodation, and multiple functions of the devices.

The ratio between the height of the accommodated ring-shaped drape portion and the corresponding length of the extended drape portion in an axial direction may be between 1/50 and 1/150, or between 1/75 and 1/125. The drape may have a length between 1800 mm and 3000 mm. The drape may be made of a film material with a thickness between 0.02 mm and 0.06 mm. The first opening, the second opening and/or the opening of an accommodated ring-shaped drape portion may have at least one diameter of more than 50 mm, or more than 70 mm.

Furthermore, in embodiments, the present disclosure relates to a method for manufacturing a device that may comprise a tubular drape and a container. The method may comprise the steps of arranging or threading a bottom container part on a mandrel, arranging or threading the drape on the mandrel, arranging or threading an upper container part on the mandrel and on a portion of the drape, wherein a substantial portion of the drape may be between the upper container part and the lower container part and at least one end portion of the drape may be outside of the container parts. Further steps may comprise compressing the drape in an axial direction between the upper container part and the lower container part, closing the container, and separating the device and mandrel. These steps may be performed in the above-given order. However, the order may also be altered. In further embodiments, the present disclosure relates to methods and procedure for covering surgical equipment, such as cameras for endoscopic use and camera cables, with devices according to the embodiments described.

A tubular drape may be of a flexible material, in some embodiments a film material. An upper and bottom container part may each be of a sheet material, either of a stiff or solid or of a flexible, e.g., film-like material. Both container parts may have openings allowing to arrange or thread them on a mandrel.

A mandrel may be a cylindrical manufacturing tool. It may be attached to a work desk or the like. It may be variable in height, also for variation during device manufacturing.

Arranging or threading a bottom container part on the mandrel may involve threading the opening of the bottom container part on the tip of the mandrel and then sliding it over at least a portion of the mandrel, in some embodiments until an end position or end stopper, e.g., onto a work desk.

The tubular drape may have a length greater than that of the mandrel. Threading the drape onto the mandrel may involve threading one end of the drape on the mandrel, sliding this end along the mandrel. This end first threaded on the mandrel may be called the bottom end. It may involve threading parts or all of the drape onto the mandrel. It may involve compressing the drape in its axial direction and/or in the direction of the mandrel axis. Compressing the drape may be realized by folding or cramming the drape. Cramming may be realized by moving a tool and/or a hand in an axial direction, thereby sliding a top end in direction of a bottom end of the drape.

Arranging or threading an upper container part on the mandrel and on a portion of the drape may be realized by threading an opening of the upper container part on the mandrel and on a portion of the drape. This drape portion may comprise the upper end of the drape, which may be the opposite end of the drape compared to the lower bottom end, which was threaded onto the mandrel first. This drape portion may be around the mandrel at the given point. A substantial portion may be between the upper and the lower container part. This portion of the drape may be compressed in an axial direction between the upper container part and the lower container part.

The container may then be closed. This step may comprise welding or adhesively connecting the upper and the lower container part while the drape may be compressed in an axial direction. This may involve ultrasonic welding. Ultrasonic weld tools may also be used for drape compression.

The device and the mandrel may be separated by removing the device from the mandrel. Alternatively, or in combination, the mandrel may be removed, e.g., mechanically and/or automatically.

The drape may be attached to the container. The method may comprise the step of forming one or more joining flanges of drape material, before or after arranging or threading the drape on the mandrel. Such joining flanges may be formed by cutting one or more slots into the tubular drape. The one or more joining flanges may be attached to the lower and/or the upper container part. They may be attached inside and/or between the two. They may be threaded through the lower container part and connected to an outer face of the lower container part.

The disclosure will be further explained by referring to the figures. It is noted that the figures serve to explain certain features that may be optional to the disclosure. The figures are not to be interpreted in a limiting way and any of the features discussed by referring to the figures may occur, alone or in combination with one or more other features, in other embodiments.

DETAILED DESCRIPTION

For defined terms herein, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended to be only exemplary. Selected features of any illustrative embodiments may be incorporated into any other described embodiments unless clearly stated to the contrary.

Figure 1:
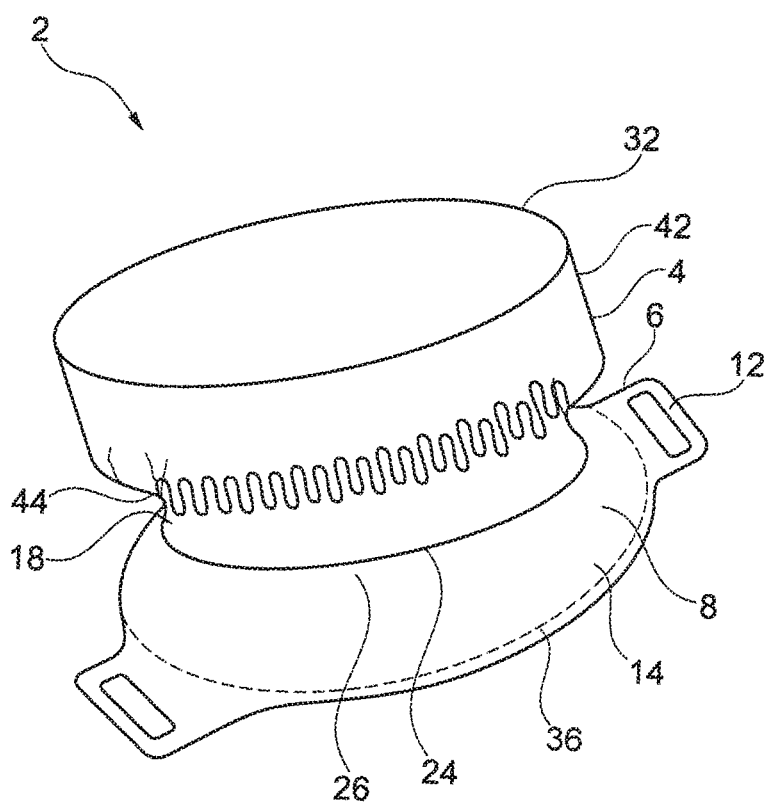
FIG. 1 shows a schematic perspective view of a device according to an embodiment of the disclosure.

FIG. 1 shows a device 2 according to an embodiment of the disclosure in a perspective view. The tubular drape 4 may extend beyond what is shown in the Figure. The second end 32 of the tubular drape 4 may be attached to a camera coupler (not shown). A drape portion 8 of drape 4 may be accommodated in the container 6. An external drape portion 42 may be outside of the container 6. The accommodated drape portion 8 may be in an axially compressed state in a ring-shape. The container may be radially inwardly open. The container may comprise a first sheet 14 and a second sheet 16 (e.g., FIG. 2). The first sheet 14 may comprise a first opening 18. The first sheet 14 may comprise a dispensing lip 24 at an edge region 26 of the first opening 18. The first sheet 14 and the second sheet 16 may be connected with a weld seam 36. The device 2 may comprise a handling portion 12, which may be formed by container 6 and which may comprise two handles located on opposite sides of the container 6. The drape 4 may be threaded through the first opening 18, forming a drape bottleneck 44. The drape bottleneck 44 may have a diameter smaller than the diameter of the tubular drape 4 in a radially expanded state. The first sheet 14 may surround an accommodated ring-shaped drape portion 8.

Figure 2:
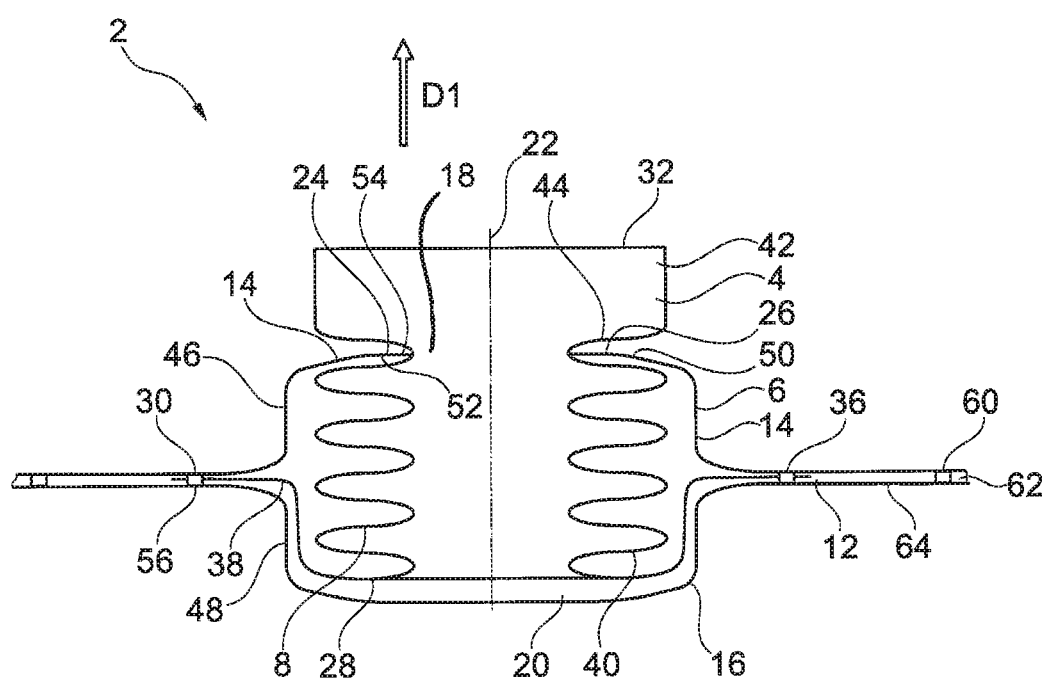
FIG. 2 shows a schematic cross-sectional view of an embodiment of the device according to the disclosure.

FIG. 2 shows a cross section of a slightly modified embodiment of the device 2 according to the disclosure. The container 6 may comprise a first sheet 14 and a second sheet 16. The first sheet 14 may comprise a first opening 18. The second sheet 16 may comprise a second opening 20. The first sheet 14 may comprise a dispensing lip 24 at an edge region 26 of the first opening 18. In this embodiment, the first sheet 14 may have a first side portion 46, the second sheet 16 may have a second side portion 48. The first side portion 46 and/or the second side portion 48 may have a cylindrical or conical shape. Otherwise, this embodiment largely corresponds to the embodiment shown in FIG. 1.

The first sheet 14 may comprise an attachment portion 30. The second sheet 16 may comprise an attachment portion 56. The first sheet 14 and the second sheet 16 may be attached to one another. A weld seam 36 may connect the two sheets. The drape 4 may be attached to the container 6. For this purpose, one or more joining flanges 38 or another part of the drape 4 may be connected the first sheet 14 and/or the second sheet 16. In some embodiments, two or more joining flanges 38 of the tubular drape 4 are welded to the first sheet 14 and the second sheet 16 with weld seam 36 at the attachment portion 30, 56. The joining flanges may correspond to the first end of the drape 28. The device may comprise a handling portion 12. The container 6 may form the handling portion 12. The handling portion 12 may comprise two handles at opposite sides of the container. One or more handling portion weld seams 60 may connect the first sheet and the second sheet. The one or more weld seams 60 may be located at an outer edge 62 of the container. The device 2 may comprise one or more non-sterile areas 64. The handling portion 12 may be a non-sterile area 64. The term "non-sterile area" does not necessarily mean that the area is not sterile, but that the area is to be used in combination with a non-sterile environment, e.g., it may be intended for contact with a non-sterile camera or the like or non-sterile surgical staff. In some embodiments, the entire device may be sterile before use.

A substantial portion 8 of the drape 4 may be accommodated inside the container 6 in an axially compressed state in a ring-shape. The accommodated portion 8 may comprise layers 40 of drape 4. These layers 40 may be symmetrical or asymmetrical and/or wrinkled. The accommodated portion 8 may alternatively or additionally be crammed. Multiple layers 40 of drape 4 may be arranged or stacked in an axial direction and/or in a radial direction. The compression of the accommodated drape portion 8 may result in compression forces in an axial direction. Such forces may correspond to forces applied to the container 6 in an axial direction. The shape of the accommodated drape portion 8 may correspond to the shape of the container 6. The first sheet 14 and/or the second sheet 16 may be of flexible material.

The drape 4 may be threaded through the first opening 18, a drape bottleneck 44 portion being between an external drape portion 42 and an accommodated drape portion 8. At the drape bottleneck 44, the drape 4 may have a bottleneck clearance 54. The drape bottleneck 44 may be an opening with a diameter of the bottleneck clearance 54, allowing for surgical equipment to be passed therethrough. The first sheet 14 may comprise a first sheet external face 50 and a first sheet internal face 52. In a compressed state in an axial direction, an accommodated drape portion may be in contact with the internal face 52. Forces, such as frictional forces, may occur between the internal face 52 and the drape. Such frictional forces may prevent drape from moving through the first opening 18. When pulling the second end 32 of drape 4 in direction D1 away from the container 6, an accommodated sub-portion of drape 4 may be withdrawn from the container 6.

The tubular drape 4 may have an axis 22. An axis of the first opening 18, an axis of the second opening 20, an axis of weld seam 36, and axis of a first side portion 46 and/or an axis of a second side portion 48 may be aligned. They may also be considered aligned, e.g., if they intersect at the device and are substantially parallel.

The container 6 may be radially inwardly open. The cross-sectional shape of the container may be described as two opposing, mirror-symmetrical "C" shapes. There are no mandrels, cores or axial walls which inwardly close the container.

Figure 3:
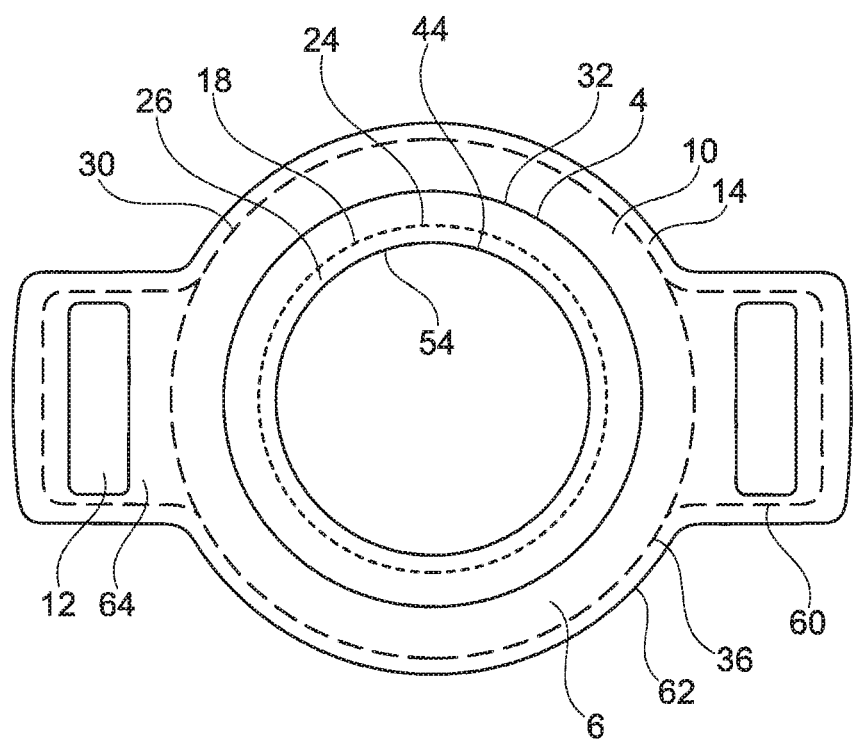
FIG. 3 shows the device of FIG. 2 in a top view.

FIG. 3 shows the device of FIG. 2 in a top view, comprising container 6 and tubular drape 4. From a top view, the first sheet 14 is visible wherein the underlying second sheet 16 is not visible in FIG. 3. Weld seams 36 and 60 may not be visible as they may be underneath the first sheet 14 in a top view. The weld seams 36 and 60 may be positioned as indicated by the dashed lines. The weld seam 36 may connect the first sheet 14 with the second sheet 16 (e.g., FIG. 2). The weld seam 36 may delimit the ring-shape 10 of an accommodated drape portion 8 (e.g., FIG. 2) in a radially outward direction. The second end 32 of the drape 4 may be outside of the container and may be part of an external drape portion 42 (e.g., FIG. 2). The drape bottleneck 44 may be between an accommodated drape portion 8 and an external drape portion 42. The bottleneck clearance 54 may define the opening of the ring-shaped accommodated drape portion 8 and/or of the device at the first opening 18. The first sheet may comprise a dispensing lip 24 at an edge region of the first opening 18. The first sheet 14 and/or the second sheet 16 may comprise an outer sheet edge 62. The device 2 may comprise a handling portion 12, which may comprise two handles symmetrically arranged oppositely. The device may comprise a non-sterile area 64. The non-sterile area 64 may be the handling portion 12. The first sheet 14 and the second sheet 16 may form the handling portion 12. The handling portion weld seam 60 may connect these two sheets at the handling portion 12. The handling portion 12 may comprise one or more material omissions such as holes, forming handles.

Figure 4A:
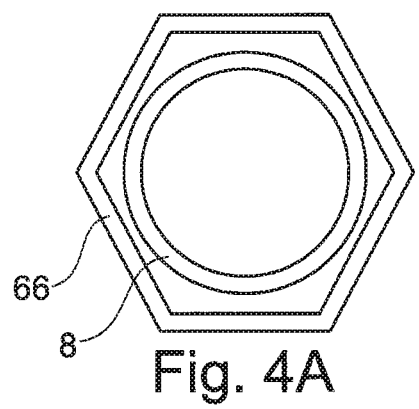
FIGS. 4A-4C show different geometries of polygon-shaped seams and accommodated drape portions of embodiments according to the disclosure.
Figure 4B:
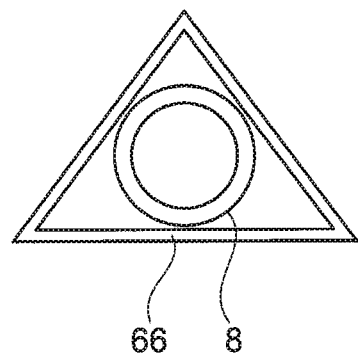
Figure 4C:
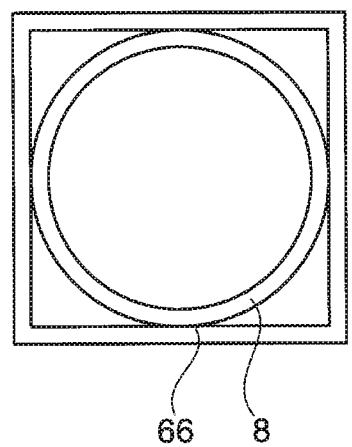

FIGS. 4A-4C show different geometries of polygon-shaped seams and accommodated drape portions 8 of embodiments according to the disclosure. A polygon-shaped seam 66 may connect a first sheet 14 (not shown) with a second sheet 16 (not shown). The seam 66 may have a polygonal shape (e.g., hexagon, triangle, or the like). The accommodated drape portion 8 may have a circular ring-shape (e.g., shape 10 in FIG. 3).

Figure 5A:
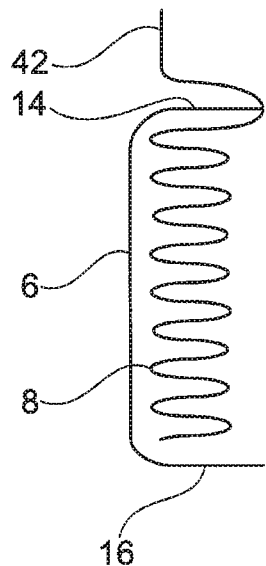
FIG. 5A shows a schematic half cross section of an embodiment of the device according to the disclosure.

FIG. 5A shows a half cross section of an embodiment of the device according to the disclosure. The container 6 may be integrally formed as one part including the first sheet 14 and the second sheet 16. In other words, the first and second sheets 14, 16 are integral and form an envelope-like configuration before closing the container. A drape portion 8 may be accommodated therein while another drape portion 42 is external with respect to the container.

Figure 5B:
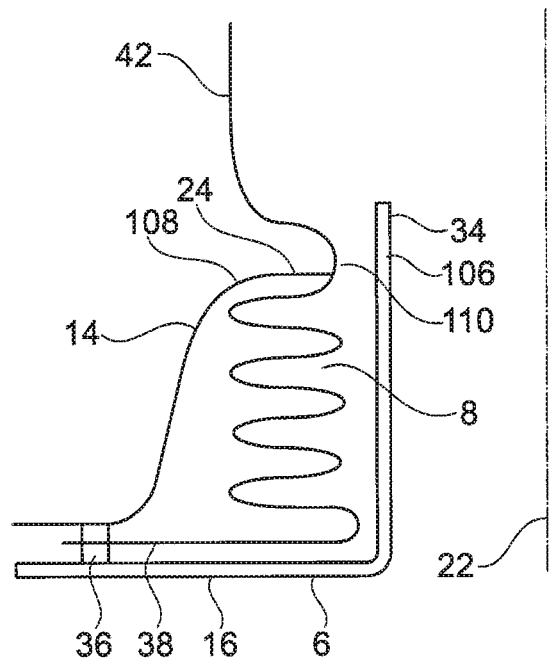
FIG. 5B shows a schematic half cross section of a further embodiment of the device according to the disclosure.

FIG. 5B shows a half-cross section of another embodiment of the device according to the disclosure. The container 6 may comprise a first sheet 14, a second sheet 16, a weld seam 36 therebetween and a container mandrel 34. A drape portion 8 may be accommodated in the container 6. The container mandrel 34 may extend from the second sheet 16 in an axial direction. The container mandrel 34 may delimit the ring-shape 10 (not shown) inwardly. From its ring-shaped accommodation within the container 6, the drape 4 may thread inwardly and axially away from the container to an external drape portion 42. The container mandrel 34 may extend beyond the first sheet 14. The second sheet 16 and the container mandrel 34 may be made from the same material and may be formed by one integral part. This integral part may be a thermoformed sheet. Said integral part may have an L-shape in a half cross section. A container mandrel 34 may correspond to an inner core 106 of the container. An outer container part 108 may be formed by the first sheet 14. A ring-shaped dispensing opening 110 may be formed between an outside of the inner core 106 of the container and an inner circumference of the dispensing lip 24 of an outer container part 108.

Figure 5C:
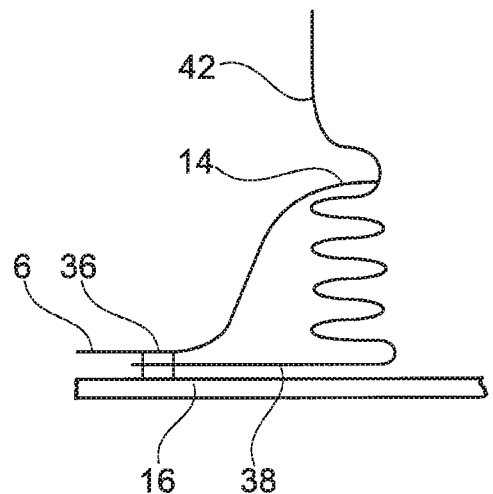
FIG. 5C shows a schematic half cross section of a further embodiment of the device according to the disclosure.

FIG. 5C shows a half cross section of another embodiment of the device according to the disclosure. In this embodiment, the second sheet 16 may be a solid or rigid sheet or at least it may be less flexible than the first sheet 14, i.e., the first sheet 14 may be more flexible. For example, the first sheet 14 may be made of a film material while the second sheet 16 may be made of a thermoformed sheet. Although FIG. 5C shows the first sheet 14 to extend more in axial direction than second sheet 16, this may be vice-versa or both may be formed with substantially symmetrical extensions. The first sheet 14, the second sheet 16 and/or joining flanges 38 of drape 4 may be connected by a weld seam 36.

Figure 5D:
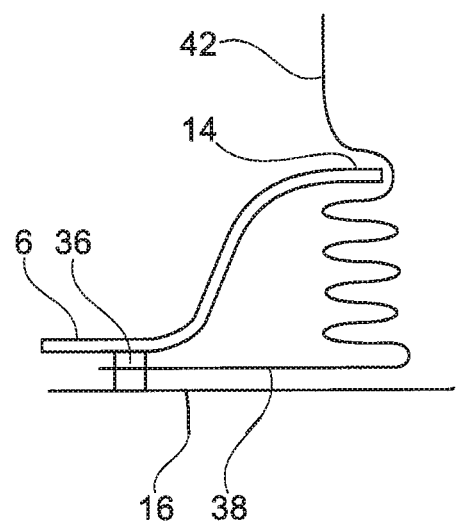
FIG. 5D shows a half schematic cross section of a further embodiment of the device according to the disclosure.

FIG. 5D shows a half cross section of another embodiment of the device according to the disclosure. In some aspects, it may be similar to FIG. 5C. In this case, however, the first sheet 14 may be a solid or rigid sheet or less flexible sheet, wherein the second sheet 16 may be more flexible. For example, the second sheet 16 may be made of a film material while the first sheet 14 may be made of a thermoformed sheet. Although FIG. 5C shows the first sheet 14 to extend more in axial direction than second sheet 16, this may be vice-versa or both may be formed with substantially symmetrical extensions.

Figure 5E:
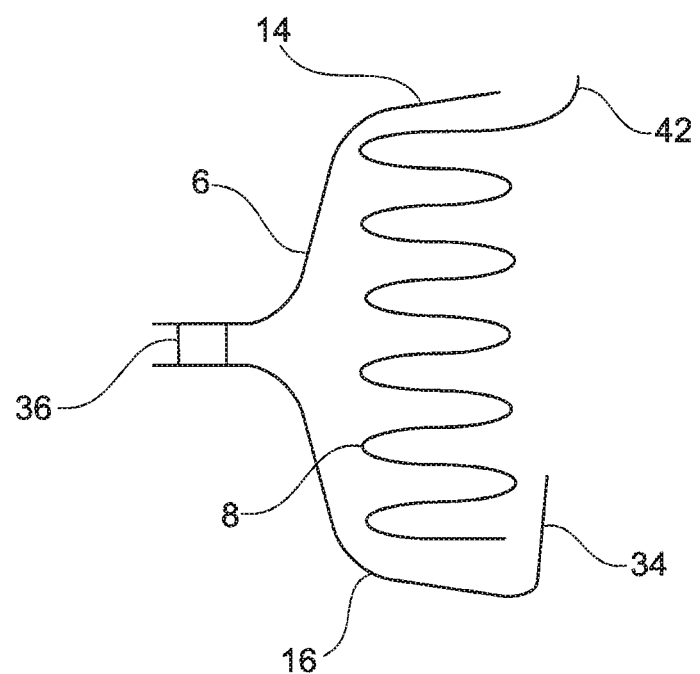
FIG. 5E shows a schematic half cross section of a further embodiment of the device according to the disclosure.

FIG. 5E shows a half cross section of another embodiment of the device according to the disclosure. The container 6 may comprise a first sheet 14, a second sheet 16 and a container mandrel 34. A drape portion 8 may be accommodated in the container 6. The container mandrel 34 may extend from the second sheet 16 in an axial direction. The container mandrel 34 may delimit the ring-shape 10 inwardly. The container 6 may be inwardly open. From its ring-shaped accommodation within the container 6, the drape 4 may thread inwardly and axially away from the container to an external drape portion 42. The container mandrel 34 does not extend up to or beyond both the first sheet 14 and the second sheet 16, hence leaving a space to open it inwardly.

Figure 6:
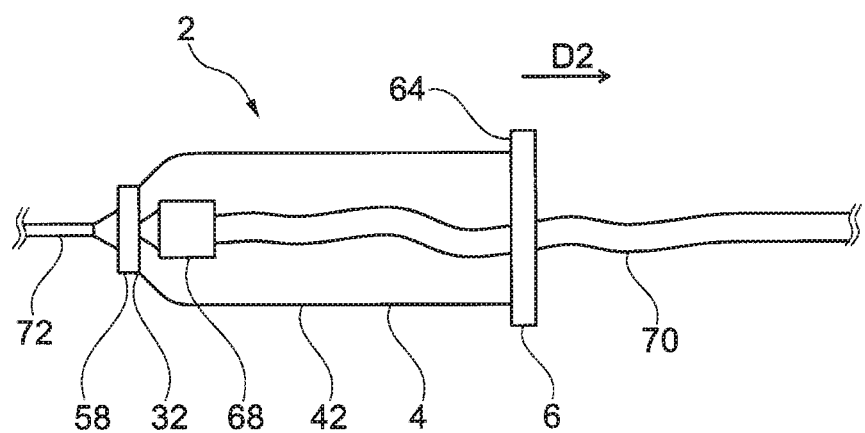
FIG. 6 shows a device according to an embodiment of the disclosure in the context of an endoscope, a camera coupler, a camera and a camera cable.

FIG. 6 shows a device according to an embodiment of the disclosure in the context of an endoscope 72 (partly shown), a camera coupler 58, a camera 68 and a camera cable 70 (partly shown). The camera coupler 58 may be attached to the second end 32 of the drape 4. The camera coupler 58 may be detachably connected to the endoscope 72 on an outer side and detachably connected to the camera 68 on an inner side. FIG. 6 shows the device in a state where the camera 68 and a part of the camera cable 70 are covered by the external portion 42 of the drape 4. The container may contain a further portion 8 (not shown) of the drape 4, accommodated within the container 6. By pulling container 6 in direction D2 away from the endoscope 72, with the second end of the drape 32 connected to the endoscope 72 via the coupler 58, further sub-portions of accommodated drape are withdrawn from the container 6. The side of the container 6 and the inside of the drape portion 42 facing the camera 68 and cable 70 may be or become non-sterile area(s) 64. The outside of the coupler 58 and the outside of the external portion 42 of the tubular drape 4 may be sterile areas. The camera 68 and the camera cable 70 may be non-sterile. Thus, the drape forms a barrier between sterile and non-sterile components.

Figure 7A:
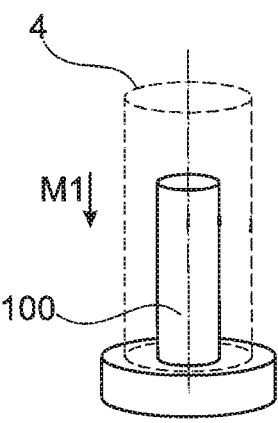
FIGS. 7A-7C show steps of a method of manufacturing according to the disclosure.
Figure 7B:
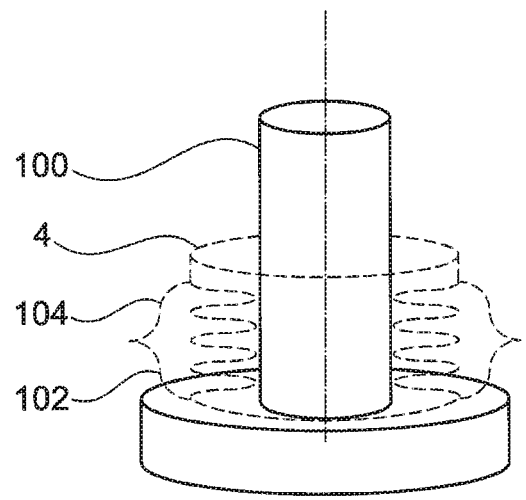
Figure 7C:
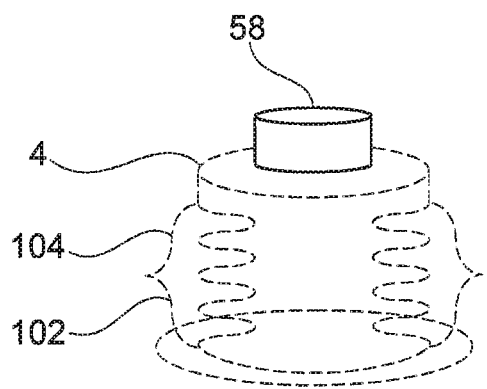

FIGS. 7A-7C show steps of a method for manufacturing a device, e.g., as described above with reference to FIGS. 1-5, according to the disclosure. FIG. 7A shows a manufacturing mandrel 100 and a tubular drape 4. The drape 4 may be arranged or threaded onto the manufacturing mandrel 100 in direction M1. The drape may be compressed in this direction.

FIG. 7B shows a manufacturing mandrel 100, a tubular drape 4, a bottom container part 102 and an upper container part 104. The drape 4 may be compressed in an axial direction between bottom container part 102 and upper container part 104. A portion of the drape which is compressed in an axial direction may be between the upper container part 104 and the lower container part 102.

FIG. 7C shows a manufactured device comprising a drape 4, a camera coupler 58, an upper container part 104 and a lower container part 102. The device may be retrieved or separated from a manufacturing mandrel. The container parts 102 and 104 may be connected. They may form one container. The camera coupler 58 may be attached to the drape 4.

Figure 8A:
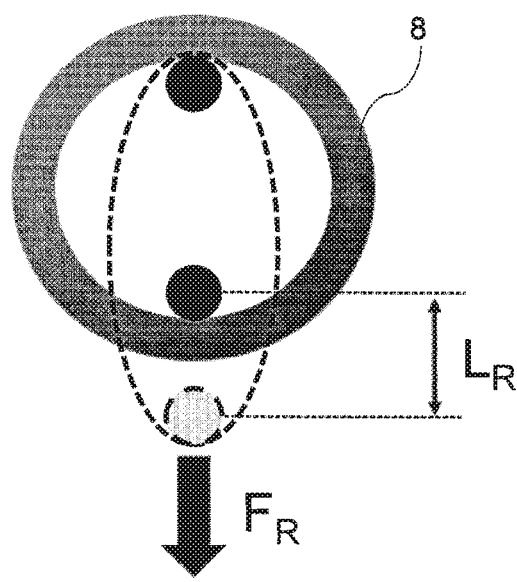
FIG. 8A shows a set-up for measuring radial stiffness of a ring-shaped drape portion.
Figures 8B, 8C:
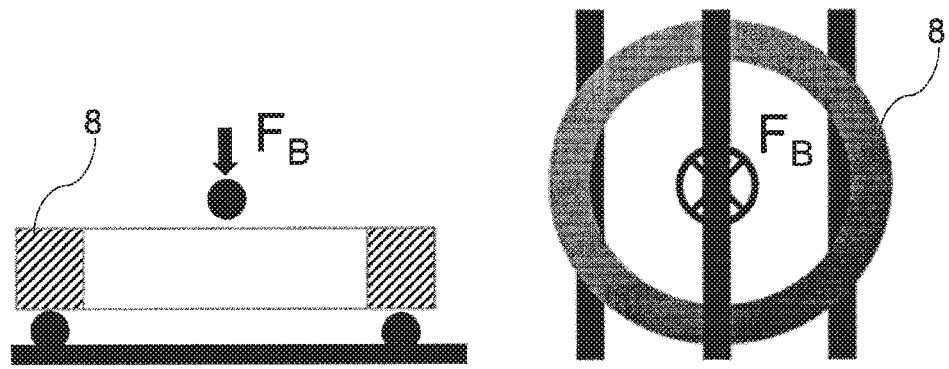
FIGS. 8B, 8C show a set-up for measuring bending stiffness of a ring-shaped drape portion.

FIG. 8A shows a set-up for measuring radial stiffness of a ring-shaped drape portion 8. FIGS. 8B and 8C show a set-up for measuring bending stiffness of a ring-shaped drape portion 8. These set-ups are not necessarily specific to the above-mentioned embodiments of the disclosure.

The tested ring-shaped drape portion 8 was made of a tubular drape section of a PE film (density 0.92 g/cm$^3$) with a length of 2.5 m and a thickness of about 0.04 mm (layflat width of about 205 mm). The diameter of the tubular drape (before converting it into a ring) was about 130 mm. The tubular drape was converted as described above in the context of FIG. 7A-7C by sliding the tubular drape over a manufacturing mandrel and cramming it down to a ring with a height of about 25 mm. The ring had an outer diameter of about 140 mm and an inner diameter of about 90 mm. The ring-shaped drape portion 8 was held in this configuration by the use of four cable ties, each at every 90 degrees, and four adhesive strips, also each every 90 degrees. The cable ties and adhesive strips were offset from each other by 45 degrees so that there was a cable tie in the middle between two adhesive strips.

The thus prepared ring-shaped drape portion 8, i.e., a "naked" ring-shaped drape portion considered without a surrounding container 6 (not shown), was tested for radial and bending stiffness quantified as follows.

The radial stiffness was measured as shown in FIG. 8A by applying a linear force $F_R$ between two opposite sides of the "naked" ring-shaped portion 8 in an outward radial direction. The following results were observed:

| Sample | Force | | | |
| --- | --- | --- | --- | --- |
| | 4 N | 6 N | 8 N | 10 N |
| Ring 1 | 0.6 mm | 1.2 mm | 1.8 mm | 2.5 mm |
| Ring 2 | 0.6 mm | 1.5 mm | 2.2 mm | 3.0 mm |

Accordingly, when applying a force $F_R$ of 4 N, the elongation or deformation distance $L_R$ of the ring-shaped drape portion remains at a maximum of about 2.5 mm, at a maximum of about 1.5 mm, or at a maximum of about 1 mm. When applying a force $F_R$ of 10 N, the elongation or deformation distance $L_R$ of the ring-shaped drape portion remains at a maximum of about 9 mm, at a maximum of about 7 mm, or at a maximum of about 5 mm.

A bending stiffness may be measured as shown in FIG. 8B and FIG. 8C. A linear force $F_B$ may be applied in a direction perpendicular to a plane of the ring-shape 10 (not shown) to two opposite points of the ring-shaped drape-portion. These points are lying on a line through the center of the ring-shape, wherein the counter-forces are applied by arranging the ring on two round supporting bars being spaced at about 105 mm from each other. Thereby, the force $F_B$ bends the opposite points downwards, while the outside points remain stationary. The following results were observed:

|        | Force   |        |        |        |
| ------ | ------- | ------ | ------ | ------ |
| Sample | 3 N     | 4 N    | 5 N    | 6 N    |
| Ring 3 | 0.8 mm  | 1.3 mm | 2.0 mm | 2.7 mm |
| Ring 4 | 0.7 mm  | 1.3 mm | 2.3 mm | 3.4 mm |

Thus, when applying a downward force $F_B$ of 3 N to the opposite points, said points move by a distance $L_B$ of about 2.5 mm or less, by about 1.5 mm or less, 1.2 mm or less. When applying a downward force $F_B$ of 6 N to the opposite points, said points move by a distance $L_B$ of about 8 mm or less, by about 6 mm or less, 4 mm or less.

In some embodiments, these aforementioned values apply to any two opposite points of the ring-shaped portion, even if it may not be of circular or exactly circular geometry.

The radial and/or bending stiffnesses of the container without an accommodated ring-shaped drape portion or with just a very short drape portion in ring-shape accommodated therein may be significantly lower than the radial and/or bending stiffnesses of the ring-shaped drape portion as quantified above.

The invention claimed is:

1. A device comprising:
    a tubular drape for covering surgical equipment; and
    a container accommodating a substantial portion of the drape in an axially compressed state in a ring-shape;
    wherein the container comprises a first flexible sheet and a second flexible sheet, wherein the first sheet and the second sheet are oppositely arranged, the first sheet having a first opening and the second sheet having a second opening, wherein the first opening is configured for withdrawal of the drape from the container, wherein the first and the second openings are configured for passing the surgical equipment to be covered therethrough, wherein an end of the drape is attached to the container, and wherein another end of the drape is free to be coupled with the surgical equipment or attached to a coupler for coupling the surgical equipment to a camera; and
    wherein the accommodated ring-shaped drape portion has a mechanical stiffness greater than a mechanical stiffness of either of the first flexible sheet and the second flexible sheet of the container.

2. The device according to claim 1, wherein the container is radially inwardly open.

3. The device according to claim 1, wherein the container has a ring-shaped dispensing opening.

4. The device according to claim 3, wherein the ring-shaped dispensing opening is formed between an outside of an inner core of the container and an inner circumference of a dispensing lip of an outer container part.

5. The device according to claim 1, wherein the drape is made of a film and/or textile material, and wherein the accommodated drape portion is folded in an axial direction and/or the accommodated drape portion is crammed to form the ring-shape.

6. The device according to claim 1, wherein the accommodated ring-shaped drape portion defines an axis, wherein an opening of the accommodated ring-shaped drape portion is configured for passing the surgical equipment therethrough, and the opening of the accommodated ring-shaped drape portion, the first opening and the second opening are substantially aligned relative to the axis.

7. The device according to claim 1, wherein the first sheet comprises a dispensing lip at an edge region of the first opening, and an attachment portion located radially outside of the dispensing lip, and wherein at the attachment portion the first sheet is connected to the second sheet.

8. The device according to claim 1, further comprising a handling portion and/or a mandrel.

9. The device according to claim 8, wherein the handling portion is formed by the container.

10. The device according to claim 1, wherein the first sheet and/or the second sheet are made of a film material and/or one or more thermoformed sheets.

11. The device according to claim 1, wherein the first sheet and the second sheet, and further container parts, are adhered or welded together, forming a closed seam, an open seam and/or multiple seams.

12. The device according to claim 1, wherein the first flexible sheet and the second flexible sheet of the container are adapted to compress the accommodated ring-shaped drape portion between the first sheet and the second sheet.

13. The device according to claim 1, wherein cross-sectional geometries of the tubular drape, the accommodated ring-shaped drape portion, the first opening and the second opening are circular, elliptical or polygonal or a combination thereof.

14. The device according to claim 1, wherein the ratio between the height of the accommodated ring-shaped drape portion and the corresponding length of the drape portion in an axial direction is in the range between and including 1/50 and 1/150.

15. The device according to claim 1, wherein the drape has a length between 1800 mm and 3000 mm and/or wherein the drape is made of a film material with a thickness between 0.02 mm and 0.06 mm.

16. The device according to claim 1, wherein the first and/or second sheet(s) are/is substantially free of perforations around their/its opening(s).

17. The device according to claim 1, wherein mechanical stiffness of the ring-shaped drape portion is such that a linear deformation of the ring-shaped drape portion when a 10 N radial force is applied is at most about 3.0 mm.

18. A method for manufacturing the device of claim 1, comprising:
    a) arranging the first sheet on a mandrel,
    b) arranging the drape on the mandrel,
    c) arranging the second sheet on the mandrel and on a portion of the drape, wherein a substantial portion of the drape is between the first sheet and the second sheet and at least one end portion of the drape is outside of the first sheet and the second sheet, d) compressing the drape in an axial direction between the first sheet and the second sheet, e) closing the first sheet and the second sheet, and f) separating the device and the mandrel.

19. The method according to claim 18, the mandrel diameter being smaller than that of the drape and smaller than or similar to an opening in the first sheet and smaller than or similar to an opening in the second sheet being configured to pass the mandrel therethrough, wherein the step of closing the first sheet and the second sheet comprises the step of welding or adhesively connecting the first sheet and the second sheet while the drape is compressed in the axial direction.

20. The method of claim 19, furthermore comprising the steps of:

a) forming one or more joining flanges of drape material, before or after arranging the drape on the mandrel, and b) joining not only the first sheet and the second sheet, but also the one or more joining flanges of the drape, wherein the one or more joining flanges are therebetween or alternatively arranged through the opening in the second sheet and connected to an outer face of the second sheet.

\* \* \* \* \*